United States Patent
Lee

(10) Patent No.: US 11,103,043 B2
(45) Date of Patent: Aug. 31, 2021

(54) CARE INSTRUMENT

(71) Applicant: Puzhen Life Co. Limited, Shatin (HK)

(72) Inventor: Andy Lee, New York, NY (US)

(73) Assignee: Puzhen Life Co., Limited, Hong Kong (HK)

( * ) Notice: Subject to any disclaimer, the term of this patent is extended or adjusted under 35 U.S.C. 154(b) by 51 days.

(21) Appl. No.: 16/534,136

(22) Filed: Aug. 7, 2019

(65) Prior Publication Data

US 2020/0260835 A1    Aug. 20, 2020

(30) Foreign Application Priority Data

Feb. 14, 2019  (CN) .......................... 201920198165.2
Feb. 14, 2019  (CN) .......................... 201920199320.2

(Continued)

(51) Int. Cl.
*B43K 5/02*     (2006.01)
*A45D 34/04*    (2006.01)
(Continued)

(52) U.S. Cl.
CPC ............. *A45D 34/04* (2013.01); *A45D 40/26* (2013.01); *A61H 1/00* (2013.01); *A61H 23/02* (2013.01);
(Continued)

(58) Field of Classification Search
CPC .......... A45D 34/04; A45D 40/26; A61H 1/00; A61H 23/02
(Continued)

(56) References Cited

U.S. PATENT DOCUMENTS 6,588,964 B1 *  7/2003  Au .......................... A45D 24/22
                                                    132/113
6,911,010 B2 *  6/2005  Dirks ................. A61H 15/0085
                                                    601/15
(Continued)

FOREIGN PATENT DOCUMENTS

CN    104771301 A    7/2015
CN    204582291 U    8/2015
(Continued)

OTHER PUBLICATIONS

U.S. Appl. No. 16/534,068, Lee, filed Aug. 7, 2019.
U.S. Appl. No. 13/534,162, Lee, filed Aug. 7, 2019.

*Primary Examiner* — Jennifer C Chiang
(74) *Attorney, Agent, or Firm* — Dorsey & Whitney LLP

(57) ABSTRACT

A care instrument arranges one or more driving components, each corresponding to a storage container stored with a care product which can be used for caring or adding aroma for the user. Each driving component takes out the care product from the corresponding storage container and transports it to the surface of the housing through one or more outlets. A control component controls the driving components to deliver the care products to the surface of the housing in a timed and quantitative manner for precise delivery of the care products. A massage component is operated in synchronization with the driving components so that the care products are transported to the surface of the housing and uniformly dispersed by the massage component for easier application to the face or the body, thereby effectively improving the user experience.

20 Claims, 7 Drawing Sheets

(30) Foreign Application Priority Data

Feb. 14, 2019 (WO) ................ PCT/CN2019/075066
Feb. 14, 2019 (WO) ................ PCT/CN2019/075067
Mar. 12, 2019 (CN) ......................... 201990000012.0
Mar. 12, 2019 (WO) ................ PCT/CN2019/077820

(51) Int. Cl.
*A61H 23/02* (2006.01)
*A45D 40/26* (2006.01)
*A61H 1/00* (2006.01)
*A61M 21/02* (2006.01)
*F04B 43/12* (2006.01)
*A61H 7/00* (2006.01)
*A45D 34/00* (2006.01)
*A61M 21/00* (2006.01)

(52) U.S. Cl.
CPC ............. *A61M 21/02* (2013.01); *F04B 43/12* (2013.01); *A45D 2034/005* (2013.01); *A45D 2200/054* (2013.01); *A45D 2200/155* (2013.01); *A45D 2200/207* (2013.01); *A61H 7/005* (2013.01); *A61H 2201/0285* (2013.01); *A61H 2201/102* (2013.01); *A61H 2201/105* (2013.01); *A61H 2205/022* (2013.01); *A61M 2021/0016* (2013.01)

(58) Field of Classification Search
USPC ........................................... 401/1, 28, 188 R
See application file for complete search history.

(56) References Cited

U.S. PATENT DOCUMENTS

| | | | | |
|---|---|---|---|---|
| 9,889,065 | B2* | 2/2018 | Sedic | ...................... A61B 5/445 |
| 10,314,763 | B2* | 6/2019 | Olkowski | ............ G09B 19/003 |
| 2008/0071202 | A1* | 3/2008 | Nardi | ................... A61B 5/6829 |
| | | | | 601/98 |
| 2012/0067977 | A1 | 3/2012 | Speigel | |
| 2014/0330289 | A1 | 6/2014 | Revivo | |

FOREIGN PATENT DOCUMENTS

| | | | |
|---|---|---|---|
| CN | 204601078 U | 9/2015 | |
| CN | 204601978 U | 9/2015 | |
| CN | 105443363 | 3/2016 | |
| CN | 105600140 A | 5/2016 | |
| CN | 207308159 U | 5/2018 | |
| CN | 108290028 | 7/2018 | |
| CN | 207898646 U | 9/2018 | |
| CN | 108968748 A | 12/2018 | |
| CN | 109259413 | 1/2019 | |
| CN | 208405744 U | 1/2019 | |
| CN | 109963611 A | 7/2019 | |
| KR | 20150010075 A | 1/2015 | |
| WO | WO 199842401 | 10/1998 | |
| WO | WO-2011015126 A1 * | 2/2011 | ............. A61H 7/005 |

\* cited by examiner

US 11,103,043 B2

CARE INSTRUMENT

CROSS-REFERENCE TO RELATED APPLICATIONS

This application is a continuation-in-part of International Patent Application No. PCT/CN2019/077820, filed on Mar. 12, 2019, a continuation-in-part of International Patent Application No. PCT/CN2019/075067, filed on Feb. 14, 2019, and a continuation-in-part of International Patent Application No. PCT/CN2019/075066, filed on Feb. 14, 2019. In addition, this application claims priority to Chinese Patent Application No. 201990000012.0, filed on Mar. 12, 2019, Chinese Patent Application No. 201920199320.2, filed on Feb. 14, 2019, and Chinese Patent Application No. 201920198165.2, filed on Feb. 14, 2019. The contents of the above-mentioned patent applications are herein incorporated by reference.

TECHNICAL FIELD

The present disclosure relates to the technical field of personal care, and in particular relates to a care instrument.

BACKGROUND

With the development of products in the field of personal care, people pay more and more attention to face and body care, from the outside appearance to the internal health. Therefore, a variety of related massage instruments have appeared on the market, but most of these massage instruments have a single massage function that is irrelevant to skin care products. Since the materials used in these massage instruments are limited generally to either plastics or metal plating, there are certain limitations in the use of some skin care products due to their pH values. Therefore, these massage instruments do not really help people get into a natural, healthy, and scientific care habit. On this basis, it is necessary to develop personal care instruments with improved technologies and healthier materials to enhance their market competitiveness and help people achieve a truly healthy scientific way of skin care.

SUMMARY

It is an object of the present disclosure to provide a care instrument which can solve the above technical problems in the prior art.

In some embodiments, to achieve the above object, the technical solutions adopted by the present disclosure include: a care instrument that includes: a housing comprising an accommodation chamber; one or more storage containers detachably attached to the housing and each containing a care product; and a massage component, one or more driving components, a control component and a power supply device arranged inside the accommodation chamber of the housing; wherein each driving component is in communication with a storage container; each storage container and its corresponding driving component are arranged at least partially inside the accommodation chamber and arranged adjacent to each other; one or more outlets in communication with the accommodation chamber are provided on the housing such that each driving component is configured to transfer the care product from a corresponding storage container and discharge the care product from the care instrument through the one or more outlets, and the power supply device is electrically connected with the massage component, each of the driving components, and the control component respectively.

In some embodiments, a temperature control component is provided in the accommodation chamber, the temperature control component is adjacent to the one or more outlets and is configured to adjust the temperature of the part of the housing that is near the one or more outlets, and the temperature control component is electrically connected with the power supply device and the control component respectively.

In some embodiments, each driving component is a compression device in communication with a corresponding storage container, and the storage container is in communication with a corresponding outlet.

In some embodiments, the compression device comprises an air compression device, or an extrusion device inserted in the storage container and capable of discharging the care product from the storage container.

In some embodiments, the air compression device is fixed at one end of the accommodation chamber, and the storage container is fixedly arranged between a corresponding air compression device and the massage component.

In some embodiments, the care instrument comprises a first conduit and a plurality of storage containers, each of the storage containers corresponds with a separate driving component, and the storage containers are all in communication with the first conduit.

In some embodiments, the care instrument comprises a first conduit in communication with one or more outlets on the housing, the first conduit comprises a main conduit and a plurality of first branch conduits in communication with the main conduit, and each of the first branch conduits is in communication with each of the storage containers.

In some embodiments, the first conduit or one of the first branch conduits has an outer diameter of 3-5 millimeters and an inner diameter of 0.5-2 millimeter.

In some embodiments, the first conduit or one of the first branch conduits has a hardness of 30A-50A as measured by an ASTM D2240 Type A Shore durometer.

In some embodiments, the care instrument comprises a first conduit in communication with one or more outlets on the housing, a plurality of outlets are provided on the housing, and the first conduit comprises a main conduit and a plurality of second branch conduits corresponding to the plurality of outlets, and each of the second branch conduits is in communication with a corresponding outlet.

In some embodiments, the first conduit or one of the second branch conduit has an outer diameter of 3-5 millimeters and an inner diameter of 0.5-2 millimeter.

In some embodiments, the control component is electrically connected with the compression device and is configured to control the operation of the compression device.

In some embodiments, each driving component is a liquid pumping device in communication with a corresponding storage container and a corresponding outlet.

In some embodiments, each liquid pumping device is arranged between a corresponding storage container and the massage component.

In some embodiments, the care instrument comprises an outlet on the housing, an inner side of the outlet is connected with the first conduit which is connected to a plurality of first branch conduits, wherein each storage container corresponds to a separate driving component, and each pair of storage container and its corresponding driving component is connected to each first branch conduit.

In some embodiments, each of the driving components is connected with the corresponding storage container through an adapting piece, and the storage container and the adapting piece are detachably connected.

In some embodiments, the housing is further provided with one or more catching grooves in communication with the accommodation chamber, each catching groove corresponds to the position of each of the one or more storage containers, and the one or more storage containers are configured to be attached to or removed from the housing through the catching grooves.

In some embodiments, the power supply device is a power source arranged inside the accommodation chamber, or a conductive device configured to be electrically connected with an external power source.

In some embodiments, the housing comprises a material selected from the group consisting of jade, quartz, tetrahertz ore, basalt, or a combination thereof.

In some embodiments, the housing has a scraping structure configured for scraping massage.

In some embodiments, the first conduit, a first branch conduit, or a second branch conduit has an outer diameter of 3-5 millimeters and an inner diameter of 0.5-2 millimeter.

In some embodiments, the first conduit, a first branch conduit, or a second branch conduit has a hardness of 30A-50A as measured by an ASTM D2240 Type A Shore durometer.

In some embodiments, the housing comprises a material selected from the group consisting of jade (e.g., green jade and white jade), quartz (e.g., rose quartz, amethyst, and green aventurine), tetrahertz ore, basalt, or a combination thereof.

In some embodiments, the massage component is a vibrator. It can provide vibration at specified frequencies, such as from 75-200 Hz. The massage component can allow the entire care instrument to vibrate. When the vibrating care instrument is applied to a user, it can help the user relax, increase blood circulation, and facilitate the application of the care product.

In some embodiments, the massage component can be a device configured to provide illumination, weak current stimulation, temperature control adjustment, radio frequency, vibration, or other forms of care or massage on the user.

In some embodiments, the control component is a Printed Circuit Board Assembly (PCBA).

In some embodiments, the control component can adjust the pumping speed of the driving components by controlling either the current or the voltage of the driving components.

In some embodiments, the control component can adjust the vibration of the massage component by controlling either the current or the voltage of the massage component.

In some embodiments, the driving component can include a peristaltic pump, an air compression device or an extrusion device. In some embodiments, the driving component can include a fluid pump, such as a peristaltic pump or any other positive displacement pumps. In other embodiments, the driving component can include impulse pumps, velocity pumps, diaphragm pump, gear pump, bellows pump, impeller pump, gravity pumps, steam pumps, valveless pumps, or any other pumps or other device appropriate for creating liquid flow or movement.

In some embodiments, the temperature control component can be a Peltier device or a thermoelectric cooler (TEC).

In some embodiments, the temperature control component can also include a temperature sensor such that the temperature of a part of the housing can be adjusted by the temperature control component based on the input from the temperature sensor.

Compared with the prior art, by including a massage component the control component, and a power supply device that supplies power to the massage component, and the control component, the care instrument of the present disclosure can control the massage component through the control component, so as to allow a user to massage the user's face or body by using the care instrument. Further, by configuring the storage containers and the driving components, and by including in each of the storage container a care product (e.g., an essential oil) which can be used provide care (e.g., to moisturize skin or to treat skin conditions) and aroma to the user, each of the driving components can transfer the care product from the corresponding storage container, transport it to one or more outlets at the surface of the housing, and discharge it through the one or more outlets. In other words, during use, the care instrument can provide both a massage function and provide an aroma therapy to a user simultaneously. In addition, the control component can control the driving components to deliver the care product to the surface of the housing in a timed and quantitative manner, so as to realize a precise delivery of the care product. In one embodiment, the control component can control the pumping speed of the driving components via a pre-set program. In addition, when the massage component is operated in synchronization with the driving components that deliver the care product, the care product can be transported to the surface of the housing during massage and can be further uniformly dispersed by the care instrument for easier application to the face or the body, thereby effectively improving the user experience.

BRIEF DESCRIPTION OF THE DRAWINGS

In order to more clearly illustrate the technical solutions in the embodiments of the present disclosure, the drawings used in the description of the embodiments will be briefly described below. The following drawings illustrate only some embodiments of the present disclosure. The following drawings are not necessarily drawn to scale.

Figure 1:
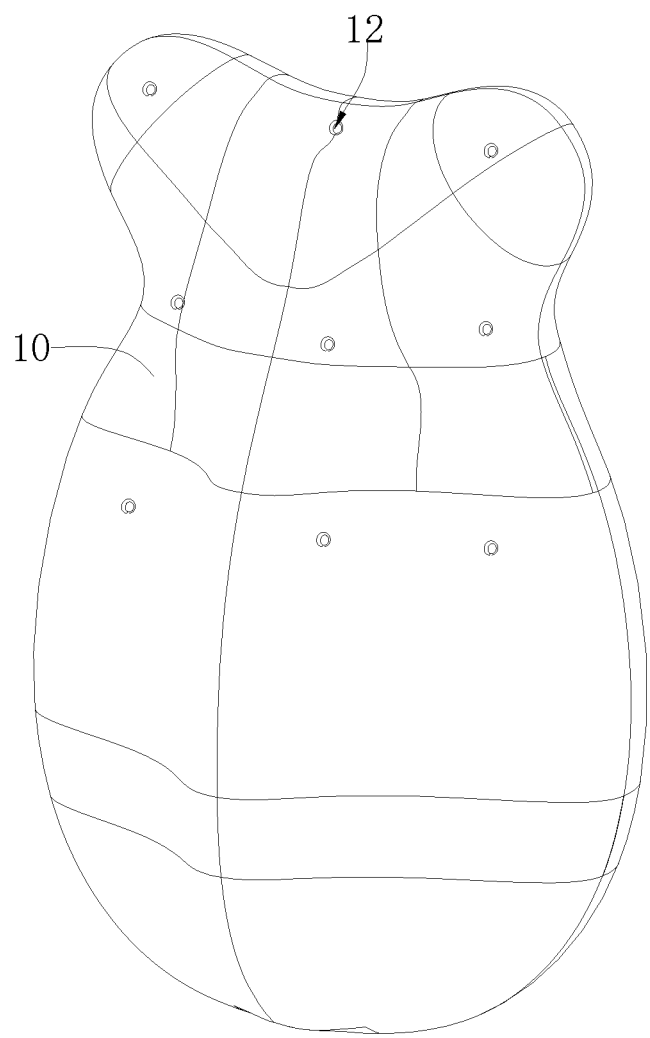
FIG. 1 is a structural schematic view of the care instrument according to an embodiment of the present disclosure.

Among them, the various reference numerals in the figures are as follows:

10: housing; 101: scraping structure; 102: docking site;
11: accommodation chamber; 12: outlet; 13: first conduit; 131: main conduit; 132: connecting conduit; 14: first branch conduit; 15: catching groove;
20: massage component; 30: driving component;
40: storage container; 41: container body; 411: adapting piece;
43: container lid; 431: pipette; 432: gravity ball;
515: Massage head; 516: First mounting body; 517: Second mounting body; 518: Third mounting body;
519: Mounting slot; 521: Thermal conducting bracket; 522: Mounting bracket;
59: Power supply device; 591: Rechargeable battery; 592: Wireless charging device;
58: Check valve; 50: control component; 70: temperature control component.

DETAILED DESCRIPTION

The embodiments of the present disclosure are described in detail below, and examples of the embodiments are illustrated in the drawings, wherein the same or similar reference numerals are used to refer to same or similar elements, or elements having the same or similar functions. The embodiments described below with reference to the accompanying FIGS. 1 to 7 are exemplary, and are intended to be illustrative of the present disclosure and are not to be construed as limiting.

In the description of the present disclosure, it should be understood that, the orientations or positional relationships indicated by the terms "length", "width", "upper", "lower", "front", "back", "left", "right", "vertical", "horizontal", "top", "bottom", "inside", "outside", etc. are based on the orientations or positional relationships shown in the drawings, which is only for the convenience of describing the present disclosure and simplifying the description, rather than to indicate or imply that the components or elements referred to have a particular orientation, or are constructed and operated in a particular orientation. Therefore, the terms are not to be construed as limiting.

Moreover, the terms "first" and "second" are used for descriptive purposes only and are not to be construed as indicating or implying a relative importance, or indicating the number of technical features referred to. Thus, the features defined with "first" and "second" may include one or more of the features either explicitly or implicitly. In the description of the present disclosure, the meaning of "a plurality of" is two or more unless explicitly and specifically defined otherwise.

In the present disclosure, the terms "connect with", "connect to", "fixed" or "fixedly" and the like shall be understood broadly, unless explicitly stated and defined otherwise. For example, the connection may refer to either fixed connection or detachable connection, or may be integrated; may refer to mechanical connection or electrical connection; may refer to direct connection, or indirect connection through an intermediate medium; may refer to internal connection between two elements, or interaction between two elements. For those skilled in the art, the specific meanings of the above terms in the present disclosure can be understood based on the specific situation.

Figure 2:
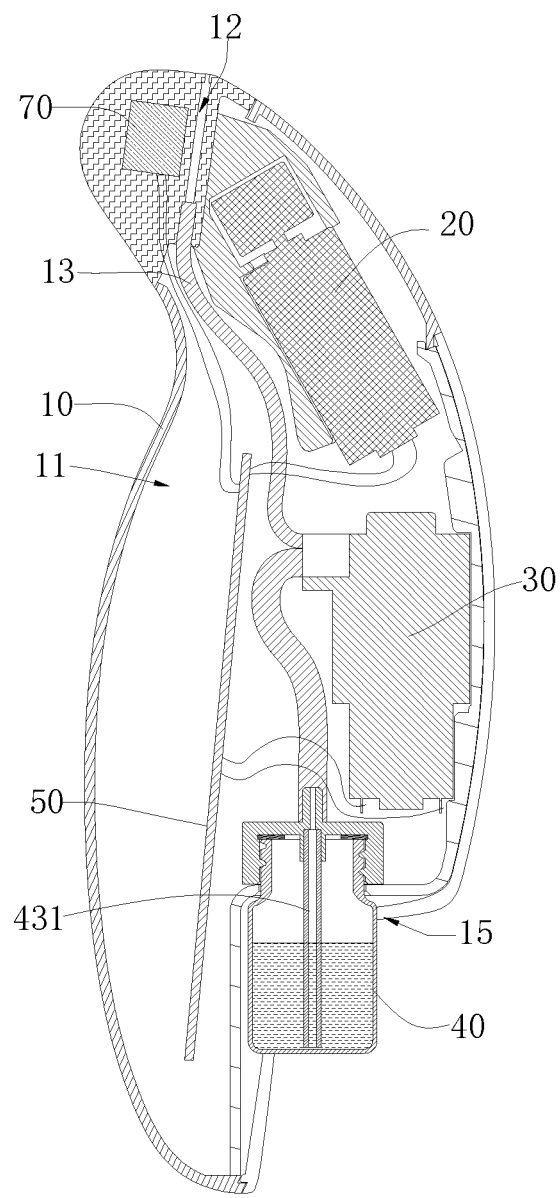
FIG. 2 is a cross-sectional structural schematic view of the care instrument according to an embodiment of the present disclosure.

As shown in FIGS. 1 and 2, an embodiment of the present disclosure provides a care instrument, which includes a housing 10, a massage component 20 arranged inside the housing 10, a driving component 30, a control component 50 and a power supply device (not shown in FIGS. 1-2). The driving component 30 is in communication (e.g., liquid fluid communication or gas fluid communication) with a storage container 40 stored with a care product (e.g., an essential oil, a medicine, a topical ointment, a cream, a perfume, a massage oil, a cosmetic product).The housing 10 is provided with an accommodation chamber 11 therein, and the storage container 40 is arranged at least partially within the accommodation chamber 11. The massage component 20 is arranged above the driving component 30 and the storage container 40. One end of the housing 10 is provided with an outlet 12 in communication (e.g., fluid communication) with the storage container 40. The driving component 30 can transfer the care product from the storage container 40 and discharge the care product through the outlet 12. The power supply device is electrically connected with the massage component 20, the driving component 30 and the control component 50, respectively, to supply power to these components.

Through providing the massage component 20, the control component 50, and the power supply device, the care instrument can control the massage component 20 through the control component 50, thereby allowing a user to massage the face or the body of the user to achieve the massage function.

Further, the storage container 40 and the driving component 30 are provided, the storage container 40 can include a care product that may be used for providing care (e.g., to moisturize skin) or fragrance or aroma to the user, and the driving component 30 can transfer the care product from the storage container 40 and transport it to the outlet 12 at the surface of the housing 10, and discharge it to the environment through the outlet 12. In this way, the care instrument in this embodiment of the present disclosure enables the user to apply the care product while using the care instrument.

Further, through controlling the driving component 30 by the control component 50, the care instrument in the embodiment of the present disclosure can deliver the care product to the surface of the housing 10 in a timed and quantitative manner, so as to achieve accurate delivery of the care product. For example, the control component 50 may control the pumping speed of the driving component 30 by controlling the current and voltage of the driving component 30 via a pre-set program. In addition, when the massage component 20 is operated in synchronization with the driving component 30 that delivers the care product, the care product can be transported to the surface of the housing 10 during massage and can be further uniformly dispersed by the care instrument for easier application to the face or the body, thereby effectively improving the user experience. Specifically, in the present embodiment, the storage container 40 is arranged adjacent to the driving component 30, such that the distance between the storage container 40 and the driving component 30 may be reduced, thereby reducing the number and the length of conduits between the storage container 40 and the driving component 30, and further reducing the volume of the care instrument.

In some embodiments, the driving component 30 is an air compression device (e.g., diaphragm air pump), or an extrusion device capable of discharging the care product from the storage container 40. When the driving component 30 is an air compression device, the air compression device is in communication with the storage container 40, and the storage container 40 is in communication with the outlet 12. By providing the driving component 30 as an air compression device, the storage compartment 40 can be inflated and pressurized by the air compression device, and then the care product stored in the storage container 40 can be pushed out and transported to the outlet 12. Moreover, since air is supplied to the storage container 40 by the air compression device to compress the care product, the air pressure inside the storage container 40 is relatively balanced.

In some embodiments, the air compression device can be operated in reverse, so that the care product located in the conduits is returned from the conduits between the storage container 40 and the outlet 12 to the storage container 40, thereby saving the care product, preventing deterioration due to prolonged exposure to the conduits, maintaining consistent care product quality throughout usage, and further avoiding the mixing of different care products in the conduits.

In some embodiments, the storage container 40 can be fixedly arranged between the air compression device and the massage component 20, so that the conduit length between the storage container 40 and the outlet 12 may be effectively reduced, which in turn reduces the length of the conduits, reducing the volume of the care instrument. In addition, reducing the distance of the conduits between the storage container 40 and the outlet 12 can reduce the time that is required from activating the care instrument by the user to dispensing the care product from the outlet 12, which can effectively improve the user experience.

In some embodiments, the housing 10 has a bottom end and top end. The outlet 12 is near the top end. When the driving component 30 is an air compression device, massage component 20 is near the top end and the air compression device is near the bottom end of housing 10.

Figure 4:
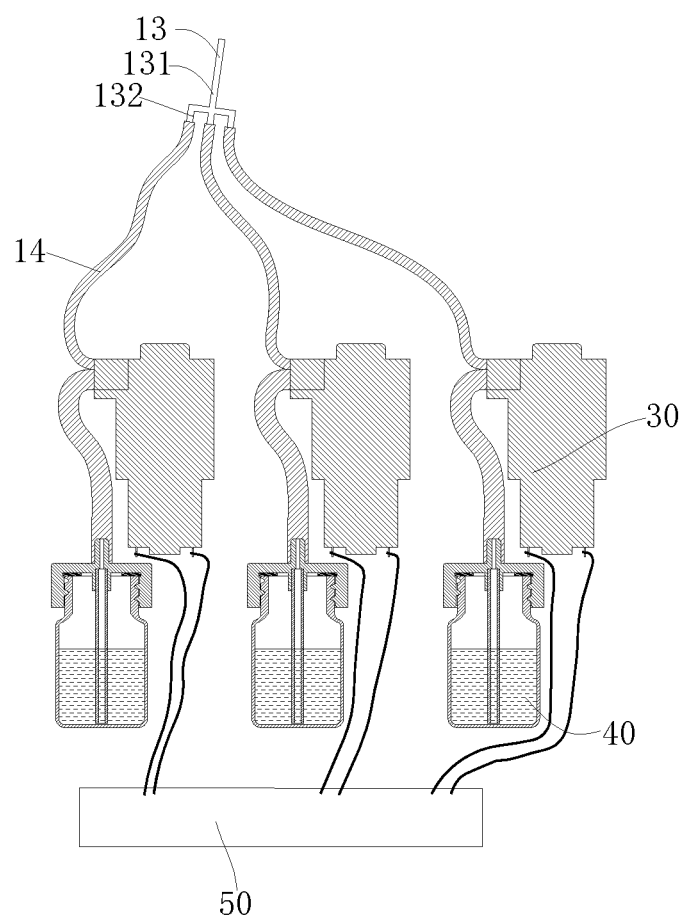
FIG. 4 is a schematic view of connection between a plurality of storage containers and a plurality of driving components of the care instrument according to an embodiment of the present disclosure.

Further, as shown in FIG. 4, in some embodiments, the inner side of the outlet 12 is connected with a first conduit 13 in communication with the outlet 12. The care instrument can include a plurality of storage containers 40 and a plurality of corresponding driving components 30 with one-to-one correspondence, and the plurality of storage containers 40 are all in communication with the first conduit 13, such that a plurality of care products of different compositions can be simultaneously pumped out by the care instrument, which is convenient for the user to use.

Further, as shown in FIG. 4, in some embodiment, the first conduit 13 includes a main conduit 131 and a plurality of first branch conduits 132 in communication with the main conduit 131, and each of the first branch conduits 132 is in communication with each of the driving component 30 and storage containers 40, respectively. Though arranging the first conduit 13 to have the main conduit 131 and the first branch conduits 132, the main conduit 131 is in communication with the outlet 12, and each of the first branch conduits 132 is in communication with one of the storage containers 40, such that the care products in the plurality of storage containers 40 can flow from storage compartments containers 40 to the outlet 12 at the same time. In this way, there can be a plurality of care products flowing out from the outlet 12 and the multiple care products can be mixed together before use, which is convenient for the user.

In some embodiments, the housing 10 is provided with a plurality of outlets 12 thereon, and the main conduit 131 is connected with a plurality of second branch conduits (not shown) corresponding to outlets 12, and each of the second branch conduits is in communication with each of the outlets 12. In this manner, the care products can be uniformly and/or simultaneously delivered to the surface of the housing 10, and the care products transported to the surface of the housing 10 can be quantitatively mixed (e.g., in a certain ratio), so as to meet the user's demand for mixing the care products.

Further, in some embodiments, the control component 50 is electrically connected to each of the driving components 30, and is capable of respectively controlling the operation of each of the driving components 30. The control component 50 is arranged to independently control each of the driving components 30, such that the user can select desired care products to be used according to his/her own need and adjust the specific amount of each of the care products, which can effectively improve the user experience. For example, the control component 50 can instruct one driving component 30 to operate while instructing other driving components 30 to stop.

Figure 3:
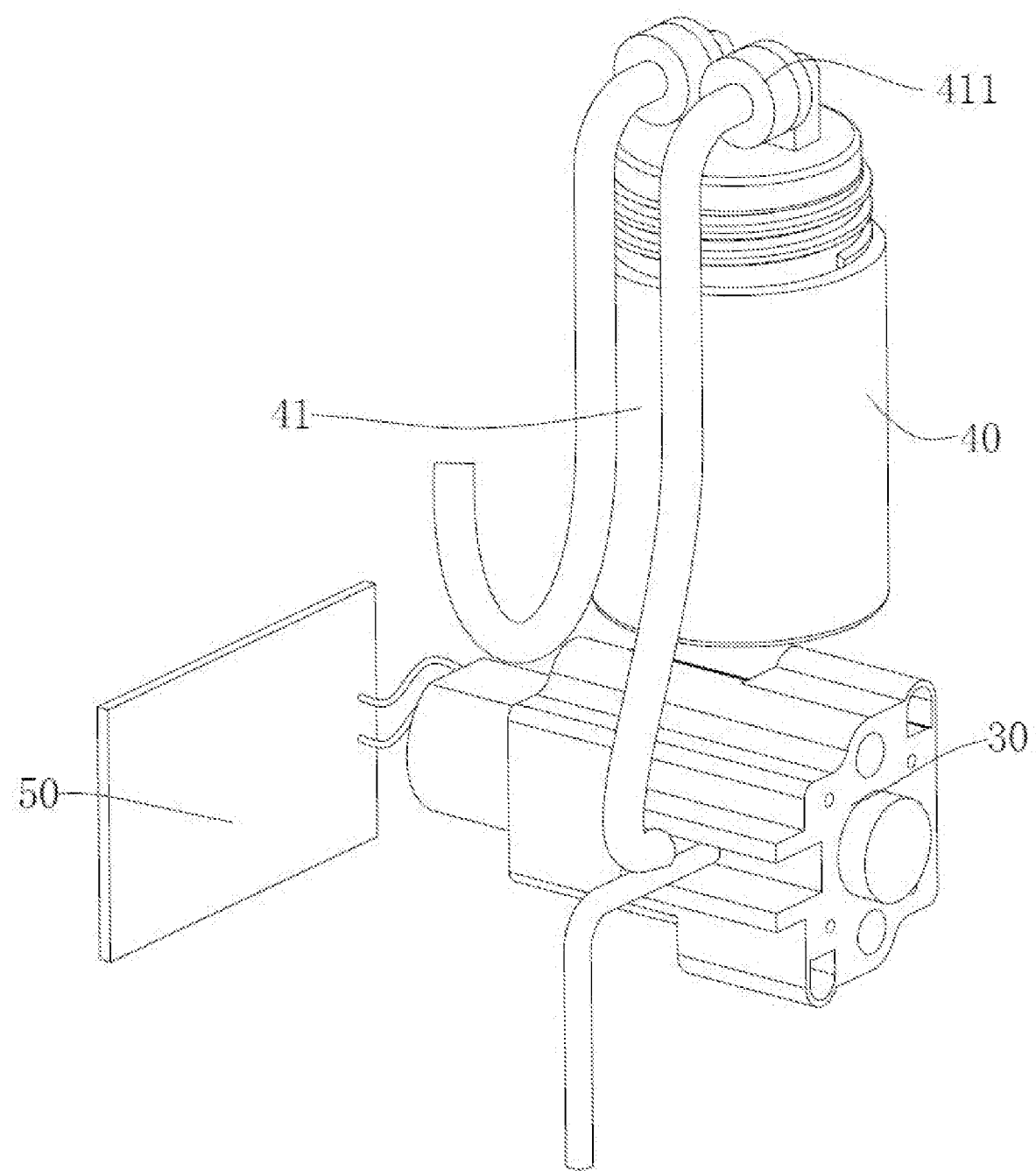
FIG. 3 is a schematic view of connection between a storage container and a driving component of the care instrument according to an embodiment of the present disclosure.

Further, as shown in FIG. 3, in the present embodiment, the driving component 30 is connected to the storage container 40 through an adapting piece 411, and the storage container 40 is detachably connected to the adapting piece 411. By arranging the storage container 40 and the adapting piece 411 to be detachably connected, the storage container 40 can be removed at any time, for example, to add a care product when the care product is used up, thereby making the care instrument be capable of long-term use, and effectively increasing the usage life of the care instrument.

Further, as shown in FIG. 2, in some embodiments, the housing 10 is further provided with a catching groove 15 in communication with the accommodation chamber 11. The catching groove 15 corresponds to the position of the storage container 40, and the storage container 40 can be attached to or removed from the catching groove 15. By providing the catching groove 15, the storage container 40 is partially exposed outside the housing 10, so that the storage container 40 may be removed when the care product needs to be added to the storage container 40.

Further, as shown in FIGS. 1 to 2, in some embodiments, one end of the accommodation chamber 11 is further provided with a temperature control component 70 for adjusting the temperature of one end of the housing 10, and the temperature control component 70 is electrically connected to the power supply device and the control component 50 respectively. By including the temperature control component 70, on the one hand, the temperature of the housing 10 of the care instrument can be adjusted according to user need when only the massage function of the care instrument is applied, so as to effectively improving the user experience; on the other hand, when the user simultaneously uses the massage function and the care function (e.g., by using a care product), the care product will be pumped out from the outlet 12 at the housing 10, such that the care product may be adjusted to a temperature suitable for use by the temperature control component 70, thereby improving the application of the care product.

Further, in some embodiments, the power supply device (not shown FIGS. 1 to 2) is a fixed power source arranged inside the accommodation chamber 11, or a conductive component able to be electrically connected with an external power source. When the power supply device is a fixed power source, it can be charged by using the external power source, so that the care instrument can be easily carried and used without an external power source. The care instrument can also be powered by using the external power source through a conductive component, so that there is no need to provide a fixed power source inside the accommodation chamber 11, thereby reducing the volume of the care instrument, miniaturizing the care instrument, reducing the weight of the care instrument, and facilitating the use by the user.

Figure 5:
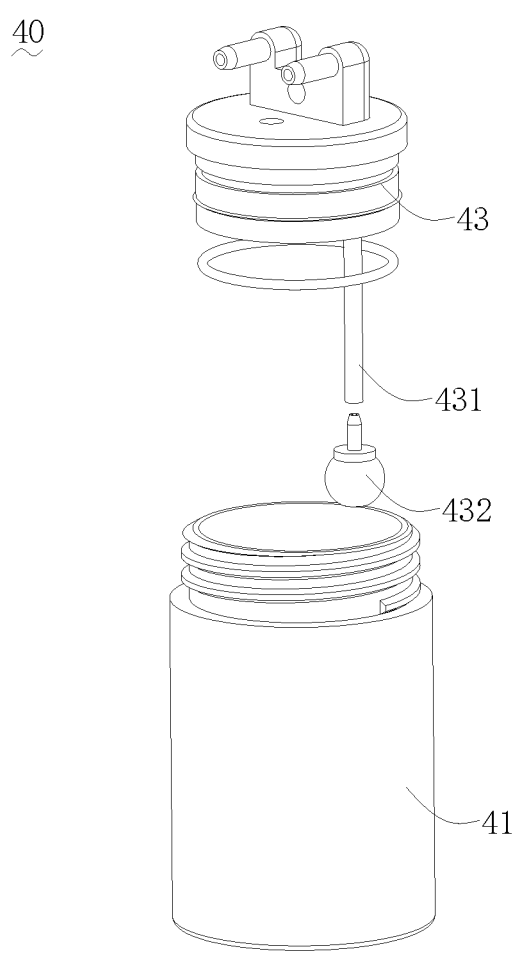
FIG. 5 is an exploded schematic view of a storage container according to an embodiment of the present disclosure.

Further, as shown in FIG. 5, in some embodiments, the storage container 40 has a container body 41 and a container lid 43 detachably connected to the container body 41. The adapting piece 411 (not shown in FIG. 5) can be fixedly connected with the container lid 43. The container body 41 and the container lid 43 are enclosed to form the storage container 40. By providing the container body 41 and the container lid 43, and arranging the container body 41 to be detachably connected with the container lid 43, the container body 41 can be detached from the can lid 43, so that the care product can be added to the storage container 40, which enables long-term use.

Further, as shown in FIG. 5, in some embodiments, the container lid 43 is provided with a pipette 431, one end of the pipette 431 is in communication with the adapting piece 411, and the other end of the pipette 431 is provided with a gravity ball 432 in connection with the pipette 431. The care instrument can change position with the user's hand during use, for example, when tilting the storage container 40. When the amount of the care product in the storage container 40 is low, the pipette may not have access to the care product. By including the pipette 431 in communication with the outlet 12 and located inside the storage container 40, the care product is led to the first conduit 13 through the pipette 431. In some embodiments, the gravity ball 432 is arranged such that the gravity ball 432 is always located at the very bottom of the storage container 40 during use (e.g., when the care instrument is tilted), that is, the gravity ball 432 is kept in contact with the care product in during use, thereby ensuring the continuity of the liquid discharge.

Further, in some embodiments, the driving component 30 is a liquid pumping device (e.g., a peristaltic pump) that is in communication with the storage container 40 and the outlet 12, respectively. For example, the liquid pumping device can be located between the storage container 40 and the outlet 12, and the liquid pumping device can transfer the care product in the storage container 40, and then transports the care product to the outlet 12. The care product can then be discharged from the housing 10 through the outlet 12 to be applied to a user.

In some embodiments, the driving component 30 is a micro pump, a peristaltic pump, or other device that can pump the care product out to the driving component 30 which then transports the care product to the outlet 12. The specific category of the driving component 30 is not limited herein.

In some embodiments, the storage container 40 is arranged at the bottom of the accommodation chamber 11, the driving component 30 is arranged above the storage container 40, and the massage component 20 is arranged above the driving component 30. By doing so, the driving component 30 can be located between the storage container 40 and the massaging component 20. In this way, the distance of between the driving component 30 and the outlet 12 can be effectively reduced, which in turn reduces the length of the conduits, as well as the volume of the care instrument. In addition, reducing the length of the conduits between the driving component 30 and the fluid outlets 12 can reduce the time that is required from activating the care instrument by the user to pumping out the care product by the outlet 12, which can effectively improve the user experience.

In some embodiments, the first conduit 13, the first branch conduits 14 and/or the second branch conduits have an outer diameter of from at least 3 mm to at most 5 mm and an inner diameter of at least 0.5 mm to at most 2 mm. The first conduit 13, the first branch conduits 14 and the second branch conduits have a hardness of 30A-50A as measured by an ASTM D2240 Type A Shore durometer. In some embodiments, the first conduit 13, the first branch conduits 14 and the second branch conduits are made of FLURAN™ F-5500-A peristaltic pump tubing. The structure and make of the first conduit 13, the first branch conduits 14 and the second branch conduits prevents blockage or corruption of the conduits. Initial testing has shown that the first conduit 13 made of FLURAN™ F-5500-A peristaltic pump tubing does not show any signs of corruption after pumping various essential oils (lemon essential oil, lavender essential oil and clover essential oil) for 24 hours, 48 hours and 56 hours at room temperature.

Figure 6:
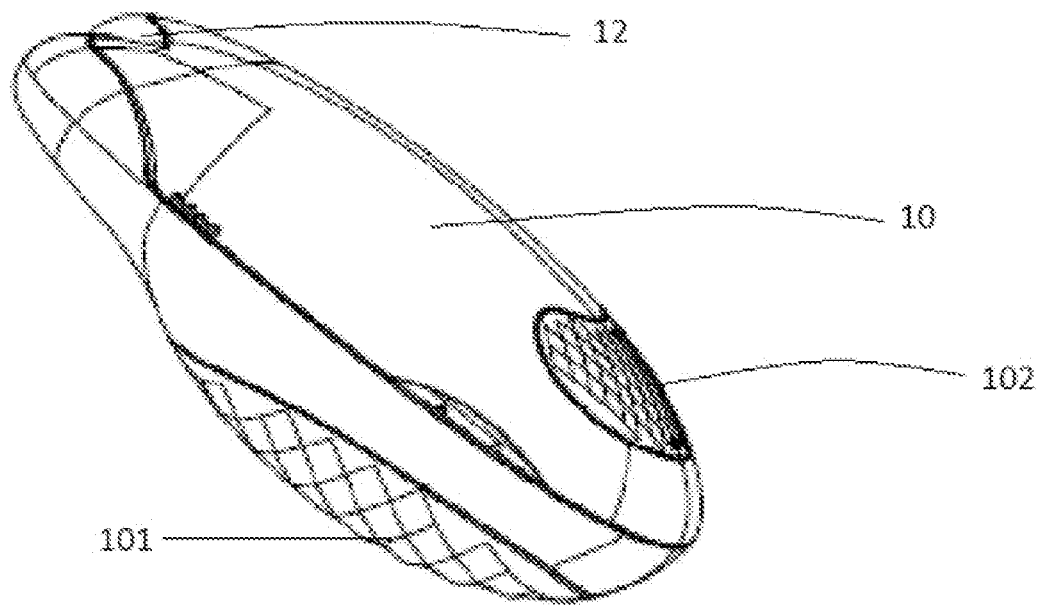
FIG. 6 is a structural schematic view of a care instrument provided by an embodiment of the present disclosure.

In some embodiments, as shown in FIG. 6, the housing 10 can include a scraping structure 101 that is suitable for scraping on a user's skin or Gua Sha. Such a scraping structure 101 can have the shape of a triangular body or a pyramid-shaped body, and can increase the surface area that is in contact with the skin. The scraping structure 101 can be connected to the house by a fixed connection such as a threaded-locking connection or a bolted connection. Scraping or Gua Sha is a part of traditional Chinese medicine. Its practitioners use a tool to apply pressure and scrape a user's skin to relive pain and tension. This action causes light bruising, which often appears as purple or red spots known as petechiae or sha. The name gua sha—pronounced gwahshah—comes from the Chinese word for scraping. It may also be called skin scraping, spooning, or coining. It helps increase blood circulation and facilitate the application of the care product. Some physiotherapists use a version of the technique known as instrument assisted soft tissue mobilization (IASTM). Using a tool instead of the hands during a massage allows a physiotherapist to apply more pressure.

In some embodiments, the housing 10 can include a material selected from the group consisting of jade (e.g., green jade and white jade), quartz (e.g., rose quartz, amethyst, and green aventurine), tetrahertz ore, basalt, or a combination thereof. Without wishing to be bound by theory, it is believed that these materials boost circulation, tone the muscles, stimulate collagen production, and can help care products get absorbed faster. It is believed that many signs of aging can be relieved by jade rolling. For example, jade rollers can visibly uplift the cheekbones, tone the face and reduce puffiness and inflammation, one of the root causes of aging. It can also smooth fine lines, tighten sagging skin, and diminish dark under-eye circles. It is believed that jade contains a lot of trace elements, which can be absorbed and improve the immune function of the human body. It is believed that rose quartz can effectively relieve tension. It is believed that terahertz ore has good thermal conductivity. It is believed that basalt contains 26 kinds of trace elements that are beneficial for the human body, which can strengthen blood circulation, improve nervous system and hormonal system, enhance cell regeneration, and increase cell metabolism. It is believed that white jade contains trace elements, such as chromium, iron, calcium, etc., which can play a role in preventing and curing diseases. Such materials can also facilitate heat dissipation. In some embodiments, one or more of these materials (jade, quartz, tetrahertz ore, basalt, or a combination thereof) can be used to form the scraping structure 101 that is suitable for scraping or Gua Sha. Such a scraping structure 101 can have the shape of a triangular body or a pyramid shaped body, and can increase the surface area that is in contact with the skin.

In some embodiments, the housing 10 comprises hypoallergenic materials such as gold (e.g., 24 k gold). The hypoallergenic materials can be applied to the housing via electroplating.

As shown in FIG. 6, in some embodiments, the housing 10 can further include a docking site 102 for wireless charging purposes. The docking site 102 can be made of a non-metal material (e.g., plastic, glass, or rubber) and corresponds to a position of a wireless charger (e.g., a wireless docking station) outside of the care instrument. When the housing 10 is fully covered by a metal plating (e.g., 24 k gold plating), the metal plating reacts to magnetic fields and attenuates electrical fields, diminishing the efficiency of wireless charging. Thus, for efficient wireless charring, it is important to have a docking site 102 made of a non-metal material that corresponds to a position of a wireless charger. Through the docking site 102, a wireless charger can charge the care instrument without interference from the metal plating.

Figure 7:
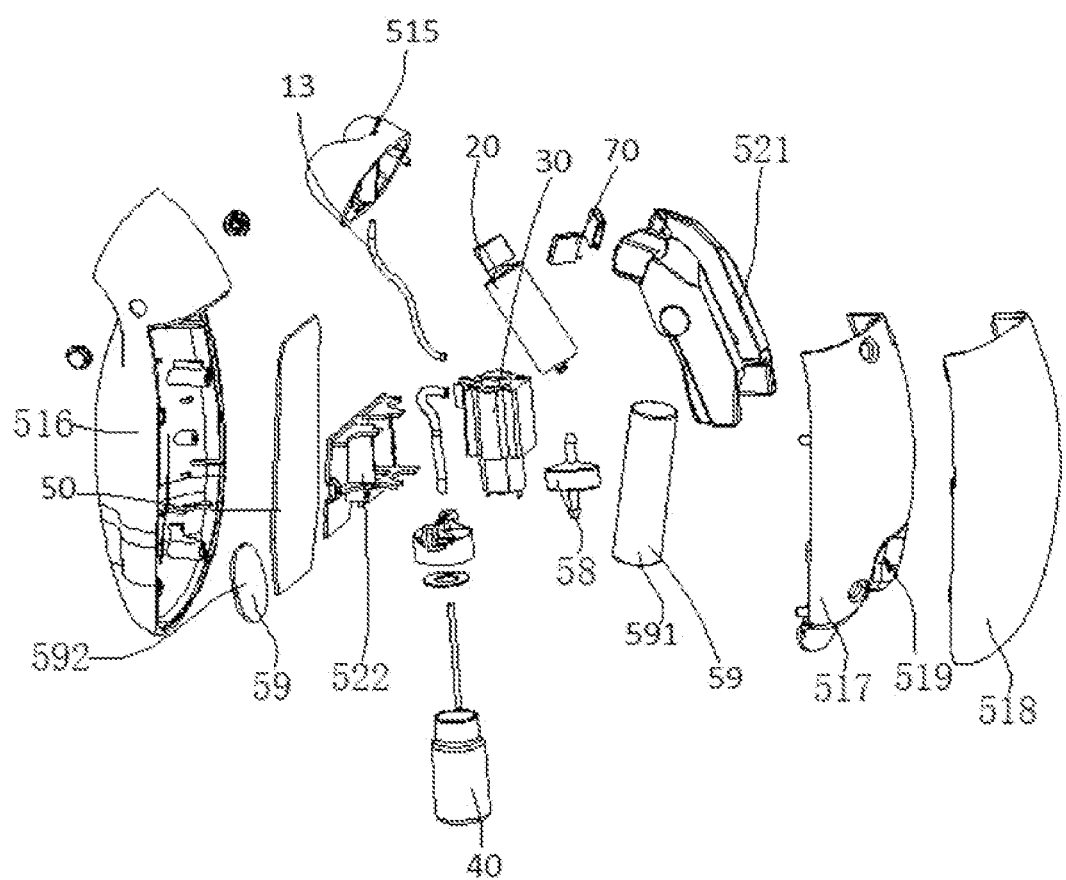
FIG. 7 is an exploded structural schematic view of a care instrument provided by an embodiment of the present disclosure.

As shown in FIG. 7, in some embodiments, the care instrument comprises: a massage head 515, a first mounting body 516, a second mounting body 517, and a third mounting body 518. The first mounting body 516, the second mounting body 517, and the massage head 515 enclose to form the housing 10. The second mounting body 517 defines therein a mounting slot 519 corresponding to a position of the storage container 40, the third mounting body 518 is detachably disposed outside the second mounting body 517 and configured to cover the mounting slot 519. By defining the mounting slot 519 at the bottom of the second mounting body 517, the storage container 40 can be mounted at or detached from the mounting slot 519, which enables the user to replace the storage container 40 in order to replace different care products, thereby satisfying different needs of the user. By further disposing the third mounting body 518 outside the second mounting body 517, the second mounting body 517 and storage container 40 can be covered by the third mounting body 518. In this way, in normal use, the user would not directly contact the storage container 40, thereby preventing the storage container 40 from falling off due to impact and improving the stability of the care instrument of the present disclosure.

As shown in FIG. 7, in some embodiments, the care instrument of the present disclosure is further provided with a power supply device 59 configured to supply power to the control component 50, the temperature control component 70, the massage component 20, and the driving component 30.

In some embodiments, as shown in FIG. 7, the power supply device 59 comprises: a rechargeable battery 591 and a wireless charging device 592 (e.g., a wireless charging coil). The wireless charging device 592 is in electrical connection with the rechargeable battery 591. The rechargeable battery 591 is in electrical connection with the control component 50, the temperature control component 70, the massage component 20, and the driving component 30, respectively. In this way, the rechargeable battery 591 can be charged by an external wireless charger (e.g., a wireless docking station) via the wireless charging device 592. In some embodiments, it is not necessary to include an additional charging interface at the surface of the care instrument, which minimize water leakage in washing the care instrument and effectively ensures the service life of the care instrument. In some embodiments, the care instrument can include a docking site 102 (as shown in FIG. 6) on the housing 10 to facilitate the charging between the external wireless charger with the wireless charging device 592.

In some embodiments, the wireless charger can be installed at or configured to fit a base of the care instrument, which can be designed to be adapted to the shape of the mounting housing of the care instrument, thereby facilitating the placement of the care instrument.

In some embodiments, the temperature control component 70 includes a Peltier device or a thermoelectric cooler (TEC) semiconductor refrigerator (not shown) and a thermal conducting bracket 521.

In some embodiments, as shown in FIG. 7, the care instrument of the present disclosure is further provided therein with the thermal conducting bracket 521 which is configured to conduct the thermal energy transmitted from the temperature control component 70 to the surface of the housing 10. The thermal conducting bracket 521 can facilitate heat transfer between the temperature control component 70 and the housing 10. By incorporating thermal conducting bracket 521, the temperature of the surface of the housing 10 can be adjusted to a required temperature, thereby satisfying the user's needs.

In some embodiments, as shown in FIG. 7, a mounting bracket 522 is further fixed in the care instrument of the present disclosure, and the storage container 40 and the driving component 30 are fixed to the mounting bracket 522. For example, the cap of the storage container 40 can be fixed at the mounting bracket 522. By providing the mounting bracket 522, the connection between storage container 40 and the driving component 30 are sufficiently firm to prevent the storage container 40 and the driving component 30 from rattling during use by the user.

In some embodiments, the control component 40 is mounted at the first mounting body 516.

The above are only preferred embodiments of the present disclosure, and are not intended to limit the present disclosure. Any modification, equivalent and improvement etc. made within the spirit and principle of the present disclosure should be included in the scope of the present disclosure.

What is claimed is:

1. A care instrument, comprising:
a housing comprising an accommodation chamber;
at least two storage containers detachably attached to the housing and each containing a care product; and
a massage component, at least two driving components, a control component and a power supply device arranged inside the accommodation chamber of the housing;
wherein:
each driving component is in communication with a storage container;
each storage container and its corresponding driving component are arranged at least partially inside the accommodation chamber and arranged adjacent to each other;
one or more outlets in communication with the accommodation chamber are provided on the housing such that each driving component is configured to transfer the care product from a corresponding storage container and discharge the care product from the care instrument through the one or more outlets, and
the power supply device is electrically connected with the massage component, each of the driving components, and the control component respectively.

2. The care instrument of claim 1, wherein a temperature control component is provided in the accommodation chamber, the temperature control component is adjacent to the one or more outlets and is configured to adjust a temperature of a part of the housing that is near the one or more outlets, and the temperature control component is electrically connected with the power supply device and the control component respectively.

3. The care instrument of claim 1, wherein each driving component is a compression device in communication with a corresponding storage container, and the storage container is in communication with a corresponding outlet.

4. The care instrument of claim 3, wherein the compression device comprises an air compression device, or an extrusion device inserted in the storage container and capable of discharging the care product from the storage container.

5. The care instrument of claim 4, wherein the control component is electrically connected with the compression device and is configured to control the operation of the compression device.

6. The care instrument of claim 5, wherein each of the driving components is connected with the corresponding storage container through an adapting piece, and the storage container and the adapting piece are detachably connected.

7. The care instrument of claim 1, wherein the care instrument comprises a first conduit in communication with one or more outlets on the housing, the first conduit comprises a main conduit and a plurality of first branch conduits in communication with the main conduit, and each of the first branch conduits is in communication with each of the storage containers.

8. The care instrument of claim 7, wherein the first conduit or one of the first branch conduits has an outer diameter of 3-5 millimeters and an inner diameter of 0.5-2 millimeter.

9. The care instrument of claim 7, wherein the first conduit or one of the first branch conduits has a hardness of 30A-50A as measured by an ASTM D2240 Type A Shore durometer.

10. The care instrument of claim 1, wherein the care instrument comprises a first conduit in communication with one or more outlets on the housing, a plurality of outlets are provided on the housing, and the first conduit comprises a main conduit and a plurality of second branch conduits corresponding to the plurality of outlets, and each of the second branch conduits is in communication with a corresponding outlet.

11. The care instrument of claim 10, wherein the first conduit or one of the second branch conduit has an outer diameter of 3-5 millimeters and an inner diameter of 0.5-2 millimeter.

12. The care instrument of claim 1, wherein each driving component is a liquid pumping device in communication with a corresponding storage container and a corresponding outlet.

13. The care instrument of claim 12, wherein each liquid pumping device is arranged between a corresponding storage container and the massage component.

14. The care instrument of claim 12, wherein the housing is further provided with one or more catching grooves in communication with the accommodation chamber, each catching groove corresponds to a position of each of the at least two storage containers, and the at least two storage containers are configured to be attached to or removed from the housing through the catching grooves.

15. The care instrument of claim 1, wherein the power supply device is a power source arranged inside the accommodation chamber, or a conductive device configured to be electrically connected with an external power source.

16. The care instrument of claim 1, wherein the housing has a scraping structure configured for scraping massage.

17. A care instrument, comprising:
a housing comprising an accommodation chamber;
one or more storage containers detachably attached to the housing and each containing a care product; and
a massage component, one or more driving components, a control component and a power supply device arranged inside the accommodation chamber of the housing;
wherein
each driving component is in communication with a storage container;
each storage container and its corresponding driving component are arranged at least partially inside the accommodation chamber and arranged adjacent to each other;
one or more outlets in communication with the accommodation chamber are provided on the housing such that each driving component is configured to transfer the care product from a corresponding storage container and discharge the care product from the care instrument through the one or more outlets, and
the power supply device is electrically connected with the massage component, each of the driving components, and the control component respectively;
wherein each driving component is a compression device in communication with a corresponding storage container, and the storage container is in communication with a corresponding outlet;
wherein the compression device comprises an air compression device, or an extrusion device inserted in the storage container and capable of discharging the care product from the storage container; and
wherein the air compression device is fixed at one end of the accommodation chamber, and the storage container is fixedly arranged between a corresponding air compression device and the massage component.

18. The care instrument of claim 17, wherein the care instrument comprises a first conduit and a plurality of storage containers, each of the storage containers corresponds with a separate driving component, and the storage containers are all in communication with the first conduit.

19. The care instrument of claim 18, wherein the care instrument comprises an outlet on the housing, an inner side of the outlet is connected with the first conduit which is connected to a plurality of first branch conduits, wherein each storage container corresponds to a separate driving component, and each pair of storage container and its corresponding driving component is connected to each first branch conduit.

20. A care instrument, comprising:
a housing comprising an accommodation chamber and a scraping structure;
one or more storage containers detachably attached to the housing and each containing a care product; and
a massage component, one or more driving components, a control component and a power supply device arranged inside the accommodation chamber of the housing;
wherein
each driving component is in communication with a storage container;
each storage container and its corresponding driving component are arranged at least partially inside the accommodation chamber and arranged adjacent to each other;
one or more outlets in communication with the accommodation chamber are provided on the housing such that each driving component is configured to transfer the care product from a corresponding storage container and discharge the care product from the care instrument through the one or more outlets, and the power supply device is electrically connected with the massage component, each of the driving components, and the control component respectively;

wherein the scraping structure comprises a material selected from the group consisting of jade, quartz, tetrahertz ore, basalt, or a combination thereof, and the scraping structure is configured to scrape a user's skin.

\* \* \* \* \*

UNITED STATES PATENT AND TRADEMARK OFFICE
CERTIFICATE OF CORRECTION

| | | |
|---|---|---|
| PATENT NO. | : 11,103,043 B2 | Page 1 of 1 |
| APPLICATION NO. | : 16/534136 | |
| DATED | : August 31, 2021 | |
| INVENTOR(S) | : Song | |

It is certified that error appears in the above-identified patent and that said Letters Patent is hereby corrected as shown below:

On the Title Page

Item (12), delete "Lee" and insert --Song--.

Item (72), 'Inventor: Andy Lee, New York, NY (US)' should be changed to: (72) --Inventor: Baojie Song, New York, NY (US)--.

Signed and Sealed this
Twenty-ninth Day of October, 2024

*Katherine Kelly Vidal*

Katherine Kelly Vidal
*Director of the United States Patent and Trademark Office*